United States Patent
Stafford

(10) Patent No.: US 8,419,753 B2
(45) Date of Patent: Apr. 16, 2013

(54) SUTURING DEVICE WITH SPLIT ARM AND METHOD OF SUTURING TISSUE

(75) Inventor: Joshua Stafford, Menlo Park, CA (US)

(73) Assignee: Abbott Laboratories, Abbott Park, IL (US)

( * ) Notice: Subject to any disclaimer, the term of this patent is extended or adjusted under 35 U.S.C. 154(b) by 825 days.

(21) Appl. No.: 12/247,012

(22) Filed: Oct. 7, 2008

(65) Prior Publication Data

US 2009/0036906 A1 Feb. 5, 2009

Related U.S. Application Data

(62) Division of application No. 10/746,210, filed on Dec. 23, 2003, now Pat. No. 7,449,024.

(51) Int. Cl.
*A61B 17/04* (2006.01)
*A61B 17/12* (2006.01)

(52) U.S. Cl.
USPC .......................................... 606/144; 606/139

(58) Field of Classification Search .................. 606/139, 606/144–148
See application file for complete search history.

(56) References Cited

U.S. PATENT DOCUMENTS

| 312,408 A | 2/1885 | Wackerhagen |
|---|---|---|
| 597,165 A | 1/1898 | Hall |
| 659,422 A | 10/1900 | Shidler |
| 989,231 A | 4/1911 | Davis |
| 1,574,362 A | 9/1922 | Callahan |
| 1,625,602 A | 4/1927 | Gould et al. |
| 1,940,351 A | 3/1933 | Howard |
| 2,012,776 A | 8/1935 | Roeder |
| 2,131,321 A | 10/1937 | Hart |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,595,086 A | 11/1948 | Larzelere |
| 2,588,589 A | 3/1952 | Tauber |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |

(Continued)

FOREIGN PATENT DOCUMENTS

| DE | 912619 | 5/1954 |
|---|---|---|
| DE | 4210724 | 7/1993 |

(Continued)

OTHER PUBLICATIONS

Grossman, William. Cardiac Catheterization and Angioplasty, 3rd Ed., Lea and Febiger. Philadelphia: 1986.

(Continued)

*Primary Examiner* — Gary Jackson
*Assistant Examiner* — Michael Mendoza
(74) *Attorney, Agent, or Firm* — Workman Nydegger; Randy Shen

(57) ABSTRACT

A device for suturing an opening in a tissue, having an elongated shaft, at least two arms movable to a deployed positioning which the arms are non-perpendicular to the shaft, the arms having needle receiving portions; and needles advanceable longitudinally along the shaft toward the needle receiving portions, the needles exiting through side walls of the shaft at a location proximal to the arms.

13 Claims, 7 Drawing Sheets

U.S. PATENT DOCUMENTS

| | | |
|---|---|---|
| 3,033,156 A | 5/1962 | Verlish |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleishhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Orvil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yo on |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,242,427 A | 9/1993 | Bilweis |
| 5,250,033 A | 10/1993 | Evans et al. |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bognato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |

| | | | | | | |
|---|---|---|---|---|---|---|
| 5,354,312 A | 10/1994 | Brinkerhoff et al. | | 5,567,435 A | 10/1996 | Hubbell et al. |
| 5,364,407 A | 11/1994 | Poll | | 5,569,269 A | 10/1996 | Hart et al. |
| 5,364,408 A | 11/1994 | Gordon | | 5,569,271 A | 10/1996 | Hoel |
| 5,368,595 A | 11/1994 | Lewis | | 5,571,120 A | 11/1996 | Yoon |
| 5,368,601 A | 11/1994 | Sauer et al. | | 5,573,540 A | 11/1996 | Yoon |
| 5,374,275 A | 12/1994 | Bradley et al. | | 5,584,842 A | 12/1996 | Fogarty et al. |
| 5,374,278 A | 12/1994 | Chesterfield et al. | | 5,591,177 A | 1/1997 | Lehrer |
| 5,376,096 A | 12/1994 | Foster | | 5,591,179 A | 1/1997 | Edelstein |
| 5,383,896 A | 1/1995 | Gershony et al. | | 5,591,206 A | 1/1997 | Moufarrege |
| 5,383,905 A | 1/1995 | Golds et al. | | 5,593,421 A | 1/1997 | Bauer |
| 5,385,569 A | 1/1995 | Swor | | 5,601,572 A | 2/1997 | Middleman et al. |
| 5,387,221 A | 2/1995 | Bisgaard | | 5,603,718 A | 2/1997 | Xu |
| 5,387,227 A | 2/1995 | Grice | | 5,607,435 A | 3/1997 | Sachdeva et al. |
| 5,391,176 A | 2/1995 | de la Torre | | 5,609,597 A | 3/1997 | Lehrer |
| 5,391,182 A | 2/1995 | Chin | | 5,611,794 A | 3/1997 | Sauer et al. |
| 5,395,332 A | 3/1995 | Ressemann et al. | | 5,613,974 A | 3/1997 | Andreas et al. |
| 5,395,349 A | 3/1995 | Quiachon et al. | | 5,613,975 A | 3/1997 | Christy |
| 5,397,310 A | 3/1995 | Chu et al. | | 5,624,446 A | 4/1997 | Harryman, II |
| 5,397,325 A | 3/1995 | Delia Badia et al. | | 5,626,588 A | 5/1997 | Sauer et al. |
| 5,397,326 A | 3/1995 | Mangum | | 5,643,289 A | 7/1997 | Sauer et al. |
| 5,403,329 A | 4/1995 | Hinchcliffe | | 5,643,295 A | 7/1997 | Yoon |
| 5,403,331 A | 4/1995 | Chesterfield et al. | | 5,643,318 A | 7/1997 | Tsukernik et al. |
| 5,403,338 A | 4/1995 | Milo | | 5,649,959 A | 7/1997 | Hannam et al. |
| 5,405,352 A | 4/1995 | Weston | | 5,662,664 A | 9/1997 | Gordon et al. |
| 5,411,481 A | 5/1995 | Allen et al. | | 5,669,917 A | 9/1997 | Sauer et al. |
| 5,413,571 A | 5/1995 | Katsaros et al. | | 5,676,689 A | 10/1997 | Kensey et al. |
| 5,417,684 A | 5/1995 | Jackson et al. | | 5,700,273 A | 12/1997 | Buelna et al. |
| 5,417,699 A | 5/1995 | Klein et al. | | 5,707,379 A | 1/1998 | Fleenor et al. |
| 5,419,765 A | 5/1995 | Weldon et al. | | 5,713,910 A | 2/1998 | Gordon et al. |
| 5,425,705 A | 6/1995 | Evard et al. | | 5,716,369 A | 2/1998 | Riza |
| 5,425,737 A | 6/1995 | Burbank et al. | | 5,720,574 A | 2/1998 | Barella |
| 5,425,740 A | 6/1995 | Hutchinson, Jr. | | 5,720,757 A | 2/1998 | Hathaway et al. |
| 5,431,666 A | 7/1995 | Sauer et al. | | 5,722,981 A | 3/1998 | Stevens |
| 5,433,700 A | 7/1995 | Peters | | 5,725,552 A | 3/1998 | Kotula et al. |
| 5,452,733 A | 9/1995 | Sterman et al. | | 5,728,109 A | 3/1998 | Schulze et al. |
| 5,454,822 A | 10/1995 | Schob et al. | | 5,728,114 A | 3/1998 | Evans et al. |
| 5,454,834 A | 10/1995 | Boebel et al. | | 5,728,133 A | 3/1998 | Kontos |
| 5,458,574 A | 10/1995 | Machold et al. | | 5,728,151 A | 3/1998 | Garrison et al. |
| 5,462,560 A | 10/1995 | Stevens | | 5,741,276 A | 4/1998 | Poloyko et al. |
| 5,462,561 A | 10/1995 | Voda | | 5,741,280 A | 4/1998 | Fleenor |
| 5,464,426 A | 11/1995 | Bonutti | | 5,746,755 A | 5/1998 | Wood et al. |
| 5,466,241 A | 11/1995 | Leroy et al. | | 5,749,890 A | 5/1998 | Shaknovich |
| 5,470,338 A | 11/1995 | Whitfield et al. | | 5,755,727 A | 5/1998 | Kontos |
| 5,474,568 A | 12/1995 | Scott | | 5,759,188 A | 6/1998 | Yoon |
| 5,476,469 A | 12/1995 | Hathaway et al. | | 5,766,183 A | 6/1998 | Sauer |
| 5,476,470 A | 12/1995 | Fitzgibbons, Jr. | | 5,766,186 A | 6/1998 | Faraz et al. |
| 5,478,309 A | 12/1995 | Sweezer et al. | | 5,766,217 A | 6/1998 | Christy |
| 5,478,353 A | 12/1995 | Yoon | | 5,769,862 A | 6/1998 | Kammerer et al. |
| 5,480,407 A | 1/1996 | Wan et al. | | 5,779,719 A | 7/1998 | Klein et al. |
| 5,486,190 A | 1/1996 | Green | | 5,782,860 A | 7/1998 | Epstein et al. |
| 5,489,295 A | 2/1996 | Piplani et al. | | 5,782,861 A | 7/1998 | Cragg et al. |
| 5,496,332 A | 3/1996 | Sierra et al. | | 5,792,151 A | 8/1998 | Heck et al. |
| 5,507,744 A | 4/1996 | Tay et al. | | 5,792,152 A | 8/1998 | Klein et al. |
| 5,507,755 A | 4/1996 | Gresl et al. | | 5,797,928 A | 8/1998 | Kogasaka |
| 5,507,757 A | 4/1996 | Sauer et al. | | 5,797,929 A | 8/1998 | Andreas et al. |
| 5,507,758 A | 4/1996 | Thomason et al. | | 5,799,661 A | 9/1998 | Boyd et al. |
| 5,509,902 A | 4/1996 | Raulerson | | 5,810,849 A | 9/1998 | Kontos |
| 5,520,655 A | 5/1996 | Davila et al. | | 5,810,850 A | 9/1998 | Hathaway et al. |
| 5,520,665 A | 5/1996 | Fleetwood | | 5,814,069 A | 9/1998 | Schulze et al. |
| 5,520,691 A | 5/1996 | Branch | | 5,817,113 A | 10/1998 | Gifford, III et al. |
| 5,520,702 A | 5/1996 | Sauer et al. | | 5,820,631 A | 10/1998 | Nobles |
| 5,527,321 A | 6/1996 | Hinchliffe | | 5,824,010 A | 10/1998 | McDonald |
| 5,527,322 A | 6/1996 | Klein et al. | | 5,824,111 A | 10/1998 | Schall et al. |
| D372,310 S | 7/1996 | Hartnett | | 5,830,125 A | 11/1998 | Scribner et al. |
| 5,531,700 A | 7/1996 | Moore et al. | | 5,836,955 A | 11/1998 | Buelna et al. |
| 5,536,273 A | 7/1996 | Lehrer | | 5,836,956 A | 11/1998 | Buelna et al. |
| 5,540,701 A | 7/1996 | Sharkey et al. | | 5,846,253 A | 12/1998 | Buelna et al. |
| 5,540,703 A | 7/1996 | Barker, Jr. et al. | | 5,848,714 A | 12/1998 | Robson et al. |
| 5,540,704 A | 7/1996 | Gordon et al. | | 5,855,585 A | 1/1999 | Kontos |
| 5,545,171 A | 8/1996 | Sharkey et al. | | 5,860,963 A | 1/1999 | Azam et al. |
| 5,545,178 A | 8/1996 | Kensey et al. | | 5,860,990 A | 1/1999 | Nobles et al. |
| 5,545,180 A | 8/1996 | Le et al. | | 5,860,991 A | 1/1999 | Klein et al. |
| 5,549,618 A | 8/1996 | Fleenor et al. | | 5,861,005 A | 1/1999 | Kontos |
| 5,549,631 A | 8/1996 | Bonutti | | 5,871,490 A | 2/1999 | Schulze et al. |
| 5,554,162 A | 9/1996 | DeLange | | 5,871,502 A | 2/1999 | Suryadevara |
| 5,562,684 A | 10/1996 | Kammerer | | 5,873,876 A | 2/1999 | Christy |
| 5,562,686 A | 10/1996 | Sauer et al. | | 5,876,411 A | 3/1999 | Kontos |
| 5,562,688 A | 10/1996 | Riza | | 5,897,487 A | 4/1999 | Ouchi |
| 5,562,728 A | 10/1996 | Lazarus et al. | | 5,897,564 A | 4/1999 | Schulze et al. |

| | | |
|---|---|---|
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford, III et al. |
| 5,906,631 A | 5/1999 | Imran |
| 5,919,207 A | 7/1999 | Taheri |
| 5,921,994 A | 7/1999 | Andreas et al. |
| 5,928,266 A | 7/1999 | Kontos |
| 5,951,590 A | 9/1999 | Goldfarb |
| 5,954,732 A | 9/1999 | Hart et al. |
| 5,957,936 A | 9/1999 | Yoon et al. |
| 5,957,937 A | 9/1999 | Yoon |
| 5,957,938 A | 9/1999 | Zhu et al. |
| 5,964,773 A | 10/1999 | Greenstein |
| 5,964,782 A | 10/1999 | Lafontaine et al. |
| 5,972,030 A | 10/1999 | Garrison et al. |
| 5,976,161 A | 11/1999 | Kirsch et al. |
| 5,980,539 A | 11/1999 | Kontos |
| 5,997,555 A | 12/1999 | Kontos |
| 6,001,109 A | 12/1999 | Kontos |
| 6,022,372 A | 2/2000 | Kontos |
| 6,024,747 A | 2/2000 | Kontos |
| 6,036,699 A | 3/2000 | Andreas et al. |
| 6,042,601 A | 3/2000 | Smith |
| 6,048,351 A | 4/2000 | Gordon et al. |
| 6,048,354 A | 4/2000 | Lawrence |
| 6,048,357 A | 4/2000 | Kontos |
| 6,068,603 A | 5/2000 | Suzuki |
| 6,077,276 A | 6/2000 | Kontos |
| 6,077,279 A | 6/2000 | Kontos |
| 6,117,144 A * | 9/2000 | Nobles et al. ................ 606/144 |
| 6,117,145 A | 9/2000 | Wood et al. |
| 6,126,675 A | 10/2000 | Shchervinsky et al. |
| 6,132,439 A | 10/2000 | Kontos |
| 6,132,440 A | 10/2000 | Hathaway et al. |
| 6,136,010 A | 10/2000 | Modesitt et al. |
| 6,139,556 A | 10/2000 | Kontos |
| 6,152,936 A | 11/2000 | Christy et al. |
| 6,165,183 A | 12/2000 | Kuehn et al. |
| 6,165,204 A | 12/2000 | Levinson et al. |
| 6,190,396 B1 | 2/2001 | Whitin et al. |
| 6,197,042 B1 | 3/2001 | Ginn et al. |
| 6,206,893 B1 | 3/2001 | Klein et al. |
| 6,206,895 B1 | 3/2001 | Levinson et al. |
| 6,245,079 B1 | 6/2001 | Nobles et al. |
| 6,248,124 B1 | 6/2001 | Pedros et al. |
| 6,296,657 B1 | 10/2001 | Brucker |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,395,015 B1 | 5/2002 | Borst et al. |
| 6,428,472 B1 | 8/2002 | Haas |
| 6,428,549 B1 | 8/2002 | Kontos |
| 6,436,109 B1 | 8/2002 | Kontos |
| 6,443,963 B1 | 9/2002 | Baldwin et al. |
| 6,451,031 B1 | 9/2002 | Kontos |
| 6,511,489 B2 | 1/2003 | Field et al. |
| 6,517,553 B2 | 2/2003 | Klein et al. |
| 6,533,812 B2 | 3/2003 | Swanson et al. |
| 6,551,330 B1 | 4/2003 | Bain et al. |
| 6,558,399 B1 | 5/2003 | Isbell et al. |
| 6,562,052 B2 | 5/2003 | Nobles et al. |
| 6,569,185 B2 | 5/2003 | Ungs |
| 6,572,629 B2 | 6/2003 | Kalloo et al. |
| 6,610,072 B1 | 8/2003 | Christy et al. |
| 6,623,509 B2 | 9/2003 | Ginn |
| 6,623,510 B2 | 9/2003 | Carley et al. |
| 6,632,237 B2 | 10/2003 | Ben-David et al. |
| 6,641,592 B1 | 11/2003 | Sauer et al. |
| 6,663,655 B2 | 12/2003 | Ginn et al. |
| 6,676,685 B2 | 1/2004 | Pedros et al. |
| 6,695,867 B2 | 2/2004 | Ginn et al. |
| 6,716,228 B2 | 4/2004 | Tal |
| 6,743,195 B2 | 6/2004 | Zucker |
| 6,743,259 B2 | 6/2004 | Ginn |
| 6,749,621 B2 | 6/2004 | Pantages et al. |
| 6,749,622 B2 | 6/2004 | McGuckin, Jr. et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,692 B2 | 5/2005 | Ginn et al. |
| 6,911,034 B2 | 6/2005 | Nobles et al. |
| 6,939,357 B2 | 9/2005 | Navarro et al. |
| 6,964,668 B2 | 11/2005 | Modesitt et al. |
| 6,969,397 B2 | 11/2005 | Ginn |
| 7,001,400 B1 | 2/2006 | Modesitt et al. |
| 7,029,480 B2 | 4/2006 | Klein et al. |
| 7,029,481 B1 | 4/2006 | Burdulis, Jr. et al. |
| 7,048,747 B2 | 5/2006 | Arcia et al. |
| 7,063,710 B2 | 6/2006 | Takamoto et al. |
| 7,083,635 B2 | 8/2006 | Ginn |
| 7,108,710 B2 | 9/2006 | Anderson |
| 7,112,225 B2 | 9/2006 | Ginn |
| 7,160,309 B2 | 1/2007 | Voss |
| 7,179,266 B2 | 2/2007 | Kontos |
| 7,229,458 B2 | 6/2007 | Boecker et al. |
| 7,235,087 B2 | 6/2007 | Modesitt et al. |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,361,183 B2 | 4/2008 | Ginn |
| 7,361,185 B2 | 4/2008 | O'Malley et al. |
| 7,377,927 B2 | 5/2008 | Burdulis, Jr. et al. |
| 7,390,328 B2 | 6/2008 | Modesitt |
| 7,393,363 B2 | 7/2008 | Ginn |
| 7,442,198 B2 | 10/2008 | Gellman et al. |
| 7,445,626 B2 | 11/2008 | Songer et al. |
| 7,449,024 B2 | 11/2008 | Stafford |
| 7,462,188 B2 | 12/2008 | McIntosh |
| 7,753,923 B2 | 7/2010 | St. Goar et al. |
| 7,837,696 B2 | 11/2010 | Modesitt et al. |
| 7,842,047 B2 | 11/2010 | Modesitt et al. |
| 7,842,048 B2 | 11/2010 | Ma |
| 7,842,049 B2 | 11/2010 | Voss |
| 7,846,170 B2 | 12/2010 | Modesitt et al. |
| 7,850,701 B2 | 12/2010 | Modesitt |
| 7,883,517 B2 | 2/2011 | Pantages et al. |
| 2001/0046518 A1 | 11/2001 | Sawhney |
| 2002/0045908 A1 | 4/2002 | Nobles et al. |
| 2002/0049453 A1* | 4/2002 | Nobles et al. ................ 606/139 |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0177876 A1 | 11/2002 | Roby et al. |
| 2003/0093093 A1 | 5/2003 | Modesitt et al. |
| 2003/0195529 A1 | 10/2003 | Takamoto et al. |
| 2004/0009205 A1 | 1/2004 | Sawhney |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0181238 A1 | 9/2004 | Zarbatany et al. |
| 2004/0186487 A1 | 9/2004 | Klein et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0267193 A1 | 12/2004 | Bagaoisan et al. |
| 2004/0267308 A1 | 12/2004 | Bagaoisan et al. |
| 2005/0059982 A1 | 3/2005 | Zung et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |

| | | | |
|---|---|---|---|
| 2006/0079914 A1 | 4/2006 | Modesitt et al. | |
| 2006/0100664 A1 | 5/2006 | Pai et al. | |
| 2006/0167477 A1 | 7/2006 | Arcia et al. | |
| 2006/0173469 A1 | 8/2006 | Klein | |
| 2006/0253037 A1 | 11/2006 | Ginn et al. | |
| 2006/0253072 A1 | 11/2006 | Pai et al. | |
| 2007/0032798 A1 | 2/2007 | Pantages et al. | |
| 2007/0032801 A1 | 2/2007 | Pantages et al. | |
| 2007/0060950 A1 | 3/2007 | Khosravi et al. | |
| 2007/0123817 A1 | 5/2007 | Khosravi et al. | |
| 2007/0276410 A1 | 11/2007 | McIntosh | |
| 2007/0282354 A1 | 12/2007 | McIntosh | |
| 2008/0009794 A1 | 1/2008 | Bagaoisan et al. | |
| 2008/0065151 A1 | 3/2008 | Ginn | |
| 2008/0065152 A1 | 3/2008 | Carley | |
| 2008/0287967 A1 | 11/2008 | Andreas et al. | |
| 2008/0319458 A1 | 12/2008 | Reynolds | |
| 2009/0005793 A1 | 1/2009 | Pantages et al. | |
| 2009/0048615 A1 | 2/2009 | McIntosh | |
| 2009/0088779 A1 | 4/2009 | Zung et al. | |
| 2009/0157105 A1 | 6/2009 | Zung et al. | |
| 2012/0053600 A1 | 3/2012 | Fortson | |

FOREIGN PATENT DOCUMENTS

| | | |
|---|---|---|
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 12/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 85/03858 | 9/1985 |
| WO | WO 01/35833 | 2/1994 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/03613 | 2/1997 |
| WO | WO 97/00046 | 3/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 02/36021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 2005/000126 | 1/2005 |
| WO | WO 2005/023119 | 3/2005 |
| WO | WO 2005/025430 | 3/2005 |
| WO | WO 2005/030060 | 4/2005 |
| WO | WO 2005/041782 | 5/2005 |
| WO | WO 2005/063129 | 7/2005 |
| WO | WO 2005/065549 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/019016 | 2/2007 |
| WO | WO 2007/081836 | 7/2007 |

OTHER PUBLICATIONS

U.S. Appl. No. 10/746,210, Mail date Apr. 5, 2007, Office Action.
U.S. Appl. No. 10/746,210, Mail date Aug. 21, 2007, Office Action.
U.S. Appl. No. 10/746,210, Mail date Jul. 9, 2008, Notice of Allowance.
U.S. Appl. No. 12/950,338, filed Nov. 19, 2010, Modesitt, et al.
U.S. Appl. No. 12/955,848, filed Nov. 29, 2010, Modesitt, et al.
U.S. Appl. No. 12/955,863, filed Nov. 29, 2010, Ma.
U.S. Appl. No. 12/955,869, filed Nov. 29, 2010, Voss.
U.S. Appl. No. 12/961,239, filed Dec. 6, 2010, Modesitt, et al.
U.S. Appl. No. 12/966,961, filed Dec. 13, 2010, Modesitt, et al.
U.S. Appl. No. 13/022,050, filed Feb. 7, 2011, Pantages et al.
U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 90/006,469, filed Nov. 29, 2002, Modesitt, et al.
US 5,820,544, 6/1974, Semm (withdrawn).
Cardio-Thoracic Systems Prospectus dated Mar. 20, 1996.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Kensey Nash Corporation, Exton, PA, "The Hemostatic Puncture Closure Device", retrieved Oct. 23, 2007, 2 pages.
Laurus Medical Corporation, "Endoscopic Suturing Made Simple," The Laurus ND-2600 Needle Driver, Irvine, CA., Oct. 1994, 1 page.
Marshall, A.C. & Lock, J.E.; "Structural and compliant anatomy of the patent foramen ovale in patients undergoing transcatheter closure", Am. Heart Journ., 140(2):303-307, Aug. 2000.
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Rema-Medizintechnik GmbH, Product Brochure entitled "REMA," Apr. 2001, 7 pages.
Serruys, PW et al., A Comparision of Balloon-Expandable-Stent Implantaion With Balloon Angioplasty in Patients With Coronary Artery Disease, New England Journal of Medicine, 331:489-495, 1994.
Taber's Cyclopedic Medical Dictionary, 18th Ed., p. 747, Feb. 1997.
U.S. Appl. No. 07/989,611, Mailed date May 12, 1993, Office Action.
U.S. Appl. No. 07/989,611, Mailed date Aug. 1, 1994, Office Action.
U.S. Appl. No. 07/989,611, Mailed date Nov. 3, 1994, Notice of Allowance.
U.S. Appl. No. 08/148,809, Mailed date Sep. 16, 1994, Office Action.
U.S. Appl. No. 08/148,809, Mailed date May 30, 1995, Office Action.

U.S. Appl. No. 08/148,809, Mailed date Dec. 15, 1995, Notice of Allowance.
U.S. Appl. No. 08/252,124, Mailed date Jun. 5, 1995, Office Action.
U.S. Appl. No. 08/252,124, Mailed date Jan. 5, 1996, Office Action.
U.S. Appl. No. 08/252,124, Mailed date May 22, 1996, Notice of Allowance.
U.S. Appl. No. 08/259,410, Mailed date Feb. 2, 1995, Office Action.
U.S. Appl. No. 08/259,410, Mailed date Jun. 1, 1995, Office Action.
U.S. Appl. No. 08/259,410, Mailed date Feb. 6, 1998, Notice of Allowance.
U.S. Appl. No. 08/638,076, Mailed date Jan. 21, 1997, Office Action.
U.S. Appl. No. 08/638,076, Mailed date Oct. 17, 1997, Notice of Allowance.
U.S. Appl. No. 08/824,031, Mailed date Mar. 16, 1998, Office Action.
U.S. Appl. No. 08/824,031, Mailed date Sep. 14, 1998, Office Action.
U.S. Appl. No. 08/824,031, Mailed date Apr. 13, 1999, Office Action.
U.S. Appl. No. 08/824,031, Mailed date Jul. 15, 1999, Notice of Allowance.
U.S. Appl. No. 08/883,246, Mailed date Jul. 23, 1998, Office Action.
U.S. Appl. No. 08/883,246, Mailed date Apr. 12, 1999, Office Action.
U.S. Appl. No. 08/883,246, Mailed date Oct. 13, 1999, Office Action.
U.S. Appl. No. 08/883,246, Mailed date Oct. 23, 2000, Office Action.
U.S. Appl. No. 08/883,246, Mailed date Jul. 11, 2001, Office Action.
U.S. Appl. No. 08/883,246, Mailed date Sep. 11, 2001, Notice of Allowance.
U.S. Appl. No. 09/057,108, Mailed date Jul. 10, 2000, Office Action.
U.S. Appl. No. 09/057,108, Mailed date Oct. 25, 2000, Notice of Allowance.
U.S. Appl. No. 09/262,402, Mailed date Mar. 29, 2000, Office Action.
U.S. Appl. No. 09/262,402, Mailed date May 30, 2000, Notice of Allowance.
U.S. Appl. No. 09/395,901, Mailed date Jun. 27, 2000, Office Action.
U.S. Appl. No. 09/395,901, Mailed date Nov. 6, 2000, Office Action.
U.S. Appl. No. 09/395,901, Mailed date Apr. 20, 2001, Notice of Allowance.
U.S. Appl. No. 09/395,901, Mailed date Sep. 10, 2001, Notice of Allowance.
U.S. Appl. No. 09/610,099, Mailed date Jul. 11, 2002, Office Action.
U.S. Appl. No. 09/610,099, Mailed date Dec. 24, 2002, Notice of Allowance.
U.S. Appl. No. 09/651,344, Mailed date Feb. 28, 2003, Office Action.
U.S. Appl. No. 09/651,344, Mailed date Nov. 7, 2003, Office Action.
U.S. Appl. No. 09/651,344, Mailed date Apr. 20, 2004, Notice of Allowance.
U.S. Appl. No. 09/707,746, Mailed date Feb. 16, 2005, Office Action.
U.S. Appl. No. 09/707,746, Mailed date Jul. 7, 2005, Office Action.
U.S. Appl. No. 09/707,746, Mailed date Nov. 15, 2005, Notice of Allowance.
U.S. Appl. No. 09/769,109, Mailed date Oct. 23, 2001, Office Action.
U.S. Appl. No. 09/769,109, Mailed date Jun. 17, 2002, Office Action.
U.S. Appl. No. 09/769,109, Mailed date Sep. 9, 2002, Notice of Allowance.
U.S. Appl. No. 09/988,541, Mailed date Mar. 17, 2004, Office Action.
U.S. Appl. No. 09/988,541, Mailed date Feb. 28, 2005, Office Action.
U.S. Appl. No. 09/988,541, Mailed date May 25, 2005, Office Action.
U.S. Appl. No. 09/988,541, Mailed date Aug. 24, 2005, Office Action.
U.S. Appl. No. 09/988,541, Mailed date Nov. 8, 2005, Office Action.
U.S. Appl. No. 09/988,541, Mailed date Dec. 13, 2005, Notice of Allowance.
U.S. Appl. No. 10/033,689, Mailed date Sep. 30, 2003, Office Action.
U.S. Appl. No. 10/152,272, Mailed date Jan. 24, 2005, Office Action.
U.S. Appl. No. 10/152,272, Mailed date May 13, 2005, Notice of Allowance.
U.S. Appl. No. 10/335,065, Mailed date Mar. 17, 2005, Office Action.
U.S. Appl. No. 10/335,065, Mailed date Jun. 10, 2005, Office Action.
U.S. Appl. No. 10/335,065, Mailed date Nov. 17, 2005, Notice of Allowance.
U.S. Appl. No. 10/335,147, Mailed date Dec. 13, 2005, Office Action.
U.S. Appl. No. 10/335,147, Mailed date Apr. 17, 2006, Office Action.
U.S. Appl. No. 10/335,147, Mailed date Oct. 4, 2006, Notice of Allowance.
U.S. Appl. No. 10/357,984, Mailed date Jan. 9, 2006, Office Action.
U.S. Appl. No. 10/357,984, Mailed date Mar. 16, 2006, Office Action.
U.S. Appl. No. 10/357,984, Mailed date Sep. 28, 2006, Office Action.
U.S. Appl. No. 10/357,984, Mailed date Mar. 23, 2007, Office Action.
U.S. Appl. No. 10/357,984, Mailed date Nov. 14, 2007, Office Action.
U.S. Appl. No. 10/652,182, Mailed date Aug. 9, 2006, Office Action.
U.S. Appl. No. 10/652,182, Mailed date Feb. 22, 2007, Notice of Allowance.
U.S. Appl. No. 10/660,288, Mailed date Nov. 15, 2005, Office Action.
U.S. Appl. No. 10/660,288, Mailed date Mar. 9, 2006, Office Action.
U.S. Appl. No. 10/660,288, Mailed date Aug. 24, 2006, Office Action.
U.S. Appl. No. 10/660,288, Mailed date Feb. 1, 2007, Office Action.
U.S. Appl. No. 10/660,288, Mailed date Jun. 28, 2007, Office Action.
U.S. Appl. No. 10/660,288, Mailed date Apr. 29, 2009, Office Action.
U.S. Appl. No. 10/660,288, Mailed date Aug. 3, 2009, Office Action.
U.S. Appl. No. 10/660,288, Mailed date Mar. 30, 2010, Office Action.
U.S. Appl. No. 10/729,541, Mailed date Dec. 12, 2006, Office Action.
U.S. Appl. No. 10/729,541, Mailed date Jun. 18, 2007, Office Action.
U.S. Appl. No. 10/729,541, Mailed date Jan. 8, 2008, Office Action.
U.S. Appl. No. 10/729,541, Mailed date Sep. 23, 2008, Office Action.
U.S. Appl. No. 10/729,541, Mailed date May 1, 2009, Office Action.
U.S. Appl. No. 10/729,541, Mailed date Nov. 16, 2009, Notice of Allowance.
U.S. Appl. No. 10/729,541, Mailed date Mar. 25, 2010, Notice of Allowance.
U.S. Appl. No. 10/729,541, Mailed date Jul. 12, 2010, Notice of Allowance.
U.S. Appl. No. 10/729,541, Mailed date Nov. 3, 2010, Issue Notification.
U.S. Appl. No. 10/737,668, Mailed date Nov. 2, 2005, Office Action.
U.S. Appl. No. 10/737,668, Mailed date Feb. 16, 2006, Office Action.
U.S. Appl. No. 10/737,668, Mailed date Oct. 19, 2006, Office Action.
U.S. Appl. No. 10/737,668, Mailed date Jun. 7, 2007, Office Action.
U.S. Appl. No. 10/737,668, Mailed date Nov. 28, 2007, Office Action.
U.S. Appl. No. 10/737,668, Mailed date Jun. 26, 2008, Notice of Allowance.
U.S. Appl. No. 10/742,406, Mailed date Mar. 23, 2007, Office Action.
U.S. Appl. No. 10/742,406, Mailed date Sep. 10, 2007, Notice of Allowance.
U.S. Appl. No. 10/742,406, Mailed date Jan. 11, 2008, Notice of Allowance.
U.S. Appl. No. 10/813,449, Mailed date Sep. 5, 2006, Office Action.
U.S. Appl. No. 10/813,449, Mailed date Jul. 16, 2007, Office Action.
U.S. Appl. No. 10/813,449, Mailed date Jan. 25, 2008, Office Action.
U.S. Appl. No. 10/813,449, Mailed date Aug. 14, 2008, Office Action.
U.S. Appl. No. 10/813,449, Mailed date Sep. 15, 2008, Office Action.
U.S. Appl. No. 10/813,449, Mailed date Feb. 3, 2009, Office Action.
U.S. Appl. No. 10/813,449, Mailed date Aug. 28, 2009, Office Action.
U.S. Appl. No. 10/813,449, Mailed date May 27, 2010, Office Action.
U.S. Appl. No. 10/909,531, Mailed date Apr. 4, 2007, Office Action.
U.S. Appl. No. 10/909,531, Mailed date Dec. 26, 2007, Office Action.
U.S. Appl. No. 10/909,531, Mailed date Jun. 13, 2008, Office Action.
U.S. Appl. No. 10/909,531, Mailed date Feb. 9, 2009, Office Action.
U.S. Appl. No. 10/909,531, Mailed date Sep. 16, 2009, Office Action.
U.S. Appl. No. 10/909,531, Mailed date Apr. 29, 2010, Notice of Allowance.
U.S. Appl. No. 10/909,531, Mailed date Aug. 20, 2010, Notice of Allowance.
U.S. Appl. No. 10/909,531, Mailed date Nov. 23, 2010, Issue Notification.
U.S. Appl. No. 10/948,445, Mailed date Jul. 11, 2007, Office Action.
U.S. Appl. No. 11/199,338, Mailed date Jan. 25, 2007, Office Action.
U.S. Appl. No. 11/199,338, Mailed date Oct. 5, 2007, Office Action.
U.S. Appl. No. 11/199,338, Mailed date Dec. 28, 2007, Office Action.
U.S. Appl. No. 11/199,338, Mailed date Apr. 23, 2008, Office Action.
U.S. Appl. No. 11/199,338, Mailed date Jan. 6, 2009, Office Action.
U.S. Appl. No. 11/199,496, Mailed date Apr. 1, 2009, Office Action.
U.S. Appl. No. 11/199,496, Mailed date Aug. 21, 2009, Office Action.
U.S. Appl. No. 11/199,496, Mailed date Apr. 23, 2010, Office Action.

U.S. Appl. No. 11/199,515, Mailed date Aug. 20, 2008, Office Action.
U.S. Appl. No. 11/199,515, Mailed date Nov. 13, 2008, Office Action.
U.S. Appl. No. 11/199,515, Mailed date Jun. 10, 2009, Office Action.
U.S. Appl. No. 11/199,515, Mailed date Dec. 24, 2009, Notice of Allowance.
U.S. Appl. No. 11/199,515, Mailed date Apr. 2, 2010, Notice of Allowance.
U.S. Appl. No. 11/199,515, Mailed date Aug. 2, 2010, Notice of Allowance.
U.S. Appl. No. 11/273,107, Mailed date Jun. 14, 2007, Office Action.
U.S. Appl. No. 11/273,107, Mailed date Jan. 18, 2008, Office Action.
U.S. Appl. No. 11/273,107, Mailed date Sep. 5, 2008, Office Action.
U.S. Appl. No. 11/273,107, Mailed date Apr. 9, 2009, Office Action.
U.S. Appl. No. 11/273,107, Mailed date Oct. 28, 2009, Office Action.
U.S. Appl. No. 11/273,107, Mailed date Jun. 2, 2010, Office Action.
U.S. Appl. No. 11/273,107, Mailed date Oct. 27, 2010, Office Action.
U.S. Appl. No. 11/363,005, Mailed date Jun. 22, 2007, Office Action.
U.S. Appl. No. 11/363,005, Mailed date Dec. 14, 2007, Office Action.
U.S. Appl. No. 11/363,005, Mailed date Apr. 17, 2008, Office Action.
U.S. Appl. No. 11/363,005, Mailed date Dec. 23, 2008, Office Action.
U.S. Appl. No. 11/363,005, Mailed date Jul. 10, 2009, Notice of Allowance.
U.S. Appl. No. 11/363,005, Mailed date Jan. 14, 2010, Notice of Allowance.
U.S. Appl. No. 11/363,005, Mailed date Jul. 23, 2010, Notice of Allowance.
U.S. Appl. No. 11/363,005, Mailed date Nov. 10, 2010, Issue Notification.
U.S. Appl. No. 11/389,762, Mailed date Sep. 20, 2007, Notice of Allowance.
U.S. Appl. No. 11/389,762, Mailed date Nov. 23, 2007, Notice of Allowance.
U.S. Appl. No. 11/390,937, Mailed date Sep. 7, 2007, Office Action.
U.S. Appl. No. 11/391,951, Mailed date Oct. 28, 2008, Office Action.
U.S. Appl. No. 11/391,951, Mailed date Jan. 30, 2009, Office Action.
U.S. Appl. No. 11/391,951, Mailed date Aug. 26, 2009, Office Action.
U.S. Appl. No. 11/391,951, Mailed date Jun. 23, 2010, Office Action.
U.S. Appl. No. 11/465,527, Mailed date Feb. 3, 2010, Office Action.
U.S. Appl. No. 11/465,527, Mailed date Jul. 23, 2010, Notice of Allowance.
U.S. Appl. No. 11/465,527, Mailed date Nov. 10, 2010, Issue Notification.
U.S. Appl. No. 11/552,593, Mailed date Aug. 21, 2008, Office Action.
U.S. Appl. No. 11/552,593, Mailed date Feb. 5, 2009, Office Action.
U.S. Appl. No. 11/552,593, Mailed date Oct. 13, 2009, Notice of Allowance.
U.S. Appl. No. 11/552,593, Mailed date Mar. 22, 2010, Notice of Allowance.
U.S. Appl. No. 11/552,593, Mailed date Jul. 22, 2010, Notice of Allowance.
U.S. Appl. No. 11/552,593, Mailed date Nov. 10, 2010, Issue Notification.
U.S. Appl. No. 11/688,722, Mailed date Mar. 10, 2010, Office Action.
U.S. Appl. No. 11/688,722, Mailed date Jul. 29, 2010, Notice of Allowance.
U.S. Appl. No. 11/688,722, Mailed date Nov. 17, 2010, Issue Notification.
U.S. Appl. No. 11/891,358, Mailed date Apr. 26, 2010, Office Action.
U.S. Appl. No. 11/891,358, Mailed date Oct. 19, 2010, Office Action.
U.S. Appl. No. 11/891,513, Mailed date Apr. 9, 2010, Office Action.
U.S. Appl. No. 11/891,513, Mailed date Sep. 28, 2010, Office Action.
U.S. Appl. No. 11/960,593, Mailed date Sep. 14, 2010, Office Action.
U.S. Appl. No. 11/960,593, Mailed date Nov. 3, 2010, Office Action.
U.S. Appl. No. 12/182,836, Mailed date Oct. 5, 2010, Office Action.
U.S. Appl. No. 12/257,127, Mailed date Aug. 30, 2010, Office Action.
U.S. Appl. No. 12/257,127, Mailed date Dec. 22, 2010, Office Action.
U.S. Appl. No. 12/334,077, Mailed date Oct. 27, 2010, Office Action.
U.S. Appl. No. 12/334,085, Mailed date Dec. 23, 2010, Office Action.
U.S. Appl. No. 90/006,469, Mailed date Nov. 29, 2002, Request for Re-Examination.
U.S. Appl. No. 90/006,469, Mailed date Sep. 10, 2004, Office Action.
U.S. Appl. No. 90/006,469, Mailed date Sep. 27, 2005, Notice of Re-Issue.
U.S. Appl. No. 90/006,469, Mailed date Jun. 27, 2006, Re-Examination Certification.
U.S. Appl. No. 10/660,288, Mailed date Mar. 29, 2011, Office Action.
U.S. Appl. No. 11/199,496, Mailed date Apr. 28, 2011, Office Action.
U.S. Appl. No. 11/960,593, Mailed date Apr. 28, 2011, Office Action.
U.S. Appl. No. 11/273,107, Mailed date Jun. 2, 2011, Notice of Allowance.
U.S. Appl. No. 12/950,338, Mailed date Jun. 15, 2011, Office Action.
U.S. Appl. No. 12/182,836, Mailed date Jun. 23, 2011, Office Action.
U.S. Appl. No. 12/955,848, Mailed date Jun. 30, 2011, Office Action.
U.S. Appl. No. 12/257,127, Mailed date Jul. 6, 2011, Office Action.
U.S. Appl. No. 11/997,379, Mailed date Jul. 13, 2011, Office Action.
U.S. Appl. No. 13/022,050, Mailed date Jul. 11, 2011, Office Action.
U.S. Appl. No. 12/334,077, Mailed date Jul. 21, 2011, Office Action.
U.S. Appl. No. 12/961,239, Mailed date Jul. 26, 2011, Notice of Allowance.
U.S. Appl. No. 12/334,085, Mailed date Aug. 4, 2011, Office Action.
U.S. Appl. No. 11/199,496, Mailed date Aug. 18, 2011, NOA.
U.S. Appl. No. 12/966,961, Mailed date Aug. 18, 2011, NOA.
U.S. Appl. No. 11/891,358, Mailed date Aug. 31, 2011, Office Action.
U.S. Appl. No. 11/891,513, Mailed date Aug. 31, 2011, Office Action.
U.S. Appl. No. 10/660,288, Mailed date Sep. 30, 2011, Notice of Allowance.
U.S. Appl. No. 11/273,107, Mailed date Sep. 28, 2011, Issue Notification.
U.S. Appl. No. 11/891,358, Mailed date Nov. 18, 2011, Office Action.
U.S. Appl. No. 11/891,513, Mailed date Nov. 1, 2011, Office Action.
U.S. Appl. No. 12/334,085, Mailed date Jan. 9, 2012, Office Action.
U.S. Appl. No. 12/950,338, Mailed date Nov. 1, 2011, Office Action.
U.S. Appl. No. 12/955,848, Mailed date Nov. 15, 2011, Office Action.
U.S. Appl. No. 12/955,863, Mailed date Jan. 6, 2012, Office Action.
U.S. Appl. No. 12/955,869, Mailed date Oct. 18, 2011, Office Action.
U.S. Appl. No. 12/257,127, Mailed date Jan. 12, 2012, Office Action.
U.S. Appl. No. 10/660,288, Mailed date Feb. 29, 2012, Issue Notification.
U.S. Appl. No. 11/997,379, Mailed date Feb. 28, 2012, Office Action.
U.S. Appl. No. 11/891,358, Mailed date Apr. 10, 2012, Notice of Allowance.
U.S. Appl. No. 11/891,513, Mailed date May 8, 2012, Notice of Allowance.
U.S. Appl. No. 12/334,085, Mailed date Apr. 18, 2012, Issue Notification.
U.S. Appl. No. 12/955,869, Mailed date Mar. 22, 2012, Notice of Allowance.
U.S. Appl. No. 13/022,050, Mailed date Apr. 26, 2012, Office Action.
U.S. Appl. No. 13/525,875, filed Jun. 18, 2012, Voss.
U.S. Appl. No. 12/950,338, mailed Aug. 8, 2012, Notice of Allowance.
U.S. Appl. No. 12/955,863, mailed May 15, 2012, Notice of Allowance.
U.S. Appl. No. 12/955,863, mailed Aug. 8, 2012, Issue Notification.
U.S. Appl. No. 13/022,050, mailed Jul. 6, 2012, Notice of Allowance.
U.S. Appl. No. 11/997,379, mailed Aug. 29, 2012, Issue Notification.
U.S. Appl. No. 12/873,728, mailed Sep. 11, 2012, Office Action.

* cited by examiner

SUTURING DEVICE WITH SPLIT ARM AND METHOD OF SUTURING TISSUE

CROSS-REFERENCE TO RELATED APPLICATIONS

This is a Divisional Application of U.S. patent application. Ser. No. 10/746,210, now U.S. Pat. No. 7,449,024, filed Dec. 23, 2003, the disclosure of which is incorporated herein by this reference.

BACKGROUND OF THE INVENTION

1. Field of the Invention

The present invention relates generally to apparatus and methods for the suturing of body lumens. More particularly, the present invention relates to techniques for percutaneous closure of arterial and venous puncture sites, which are usually accessed through a tissue tract.

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique, as described, for example, in William Grossman's "Cardiac Catheterization and Angioplasty," 3.sup.rd Ed., Lea and Febiger, Philadelphia, 1986, incorporated herein by reference. Vascular access is generally provided through an introducer sheath, which is positioned to extend from outside the patient body into the vascular lumen.

When vascular access is no longer required, the introducer sheath is removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation so as to assure continued hemostasis. During this time renewed bleeding may occur, resulting in blood loss through the tract, hematoma and/or pseudoaneurysm formation, as well as arteriovenous fistula formation. These complications may require blood transfusion and/or surgical intervention.

The incidence of complications from compression-induced hemostasis increases when the size of the introducer sheath grows larger, and/or when the patient is anticoagulated. It is clear that the compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel. Locating the fastener too far from that interface can result in failure to provide hemostasis, and subsequent hematoma and/or pseudo-aneurysm formation. Conversely, if the sealing body intrudes into the arterial lumen, intravascular clots and/or collagen pieces with thrombus attached can form and embolize downstream, causing vascular occlusion. Also, thrombus formation on the surface of a sealing body protruding into the lumen can cause a stenosis, which can obstruct normal blood flow. Other possible complications include infection, as well as adverse reaction to the collagen or other implant.

A more effective approach for vascular closure has been proposed in U.S. Pat. Nos. 5,417,699, 5,613,974; and PCT published Patent Application No. PCT/US96/10271 filed on Jun. 12, 1996, the full disclosures of which are incorporated herein by reference. A suture-applying device is introduced through the tissue tract with a distal end of the device extending through the vascular puncture. One or more needles in the device are then used to draw suture through the blood vessel wall on opposite sides of the puncture, and the suture is secured directly over the adventitial surface of the blood vessel wall to provide highly reliable closure.

While a significant improvement over the use of manual pressure, clamps, and collagen plugs, certain design criteria have been found to be important to successful suturing to achieve vascular closure. For example, it is highly beneficial to properly direct the needles through the blood vessel wall at a significant distance from the puncture so that the suture is well anchored in the tissue and can provide tight closure. It is also highly beneficial to insure that the needle deployment takes place when the device is properly positioned relative to the vessel wall. The ease of deployment and efficacy of the procedure can further be enhanced by reducing the cross-section of that portion of the device, which is inserted into the tissue tract and/or the vessel itself, which may also allow closure of the vessel in a relatively short amount of time without imposing excessive injury to the tissue tract or vessel.

For the above reasons, it would be desirable to provide improved devices, systems, and methods for suturing vascular punctures. The new device should have the capability of delivering a pre-tied knot to an incision site. It would be particularly beneficial if these improved devices provided some or all of the benefits while overcoming one or more of the disadvantages discussed above.

2. Description of the Background Art

U.S. Pat. Nos. 5,700,273, 5,836,956, and 5,846,253 describe a wound closure apparatus and method in which needles are threaded with suture inside a blood vessel. U.S. Pat. No. 5,496,332 describes a wound closure apparatus and method for its use, while U.S. Pat. No. 5,364,408 describes an endoscopic suture system.

U.S. Pat. No. 5,374,275 describes a surgical suturing device and method of use, while U.S. Pat. No. 5,417,699 describes a device and method for the percutaneous suturing of a vascular puncture site. An instrument for closing trocar puncture wounds is described in U.S. Pat. No. 5,470,338, and a related device is described in U.S. Pat. No. 5,527,321. U.S. Pat. No. 5,507,757 also describes a method of closing puncture wounds.

U.S. Pat. No. 6,245,079, describes another suturing system, the complete disclosure of which is incorporated herein by reference in its entirety for all purposes.

SUMMARY OF THE INVENTION

The present invention provides a device for suturing an opening in a tissue. In various embodiments, the device includes an elongated shaft with a pair of deployable arms. When deployed, these arms are non-perpendicular to the longitudinal axis of the shaft. In one embodiment, the arms are independently deployable. In one embodiment, a first arm is an anterior arm which is deployed by being rotated less than 90 degrees to the longitudinal axis of the shaft, and the second arm is a posterior arm which is deployed by being rotated more than 90 degrees to the longitudinal axis of the shaft. A pivot stop may be provided on the elongated shaft to limit rotation of the arms when they reach their fully deployed position. Each of the first and second arms may include a needle receiving portion thereon. Needles may be advanced longitudinally along the shaft toward the needle receiving portions on the arms. The needles may exit through a sidewall of the shaft at a location proximal to the arms.

BRIEF DESCRIPTION OF THE DRAWINGS

(FIG. 1 corresponds to FIG. 41 of U.S. Pat. No. 6,245,079).

(FIG. 2 corresponds to FIG. 42 of U.S. Pat. No. 6,245,079).

(FIG. 3 corresponds to FIG. 47 of U.S. Pat. No. 6,245,079).

DETAILED DESCRIPTION OF THE PREFERRED EMBODIMENTS

Figure 1:
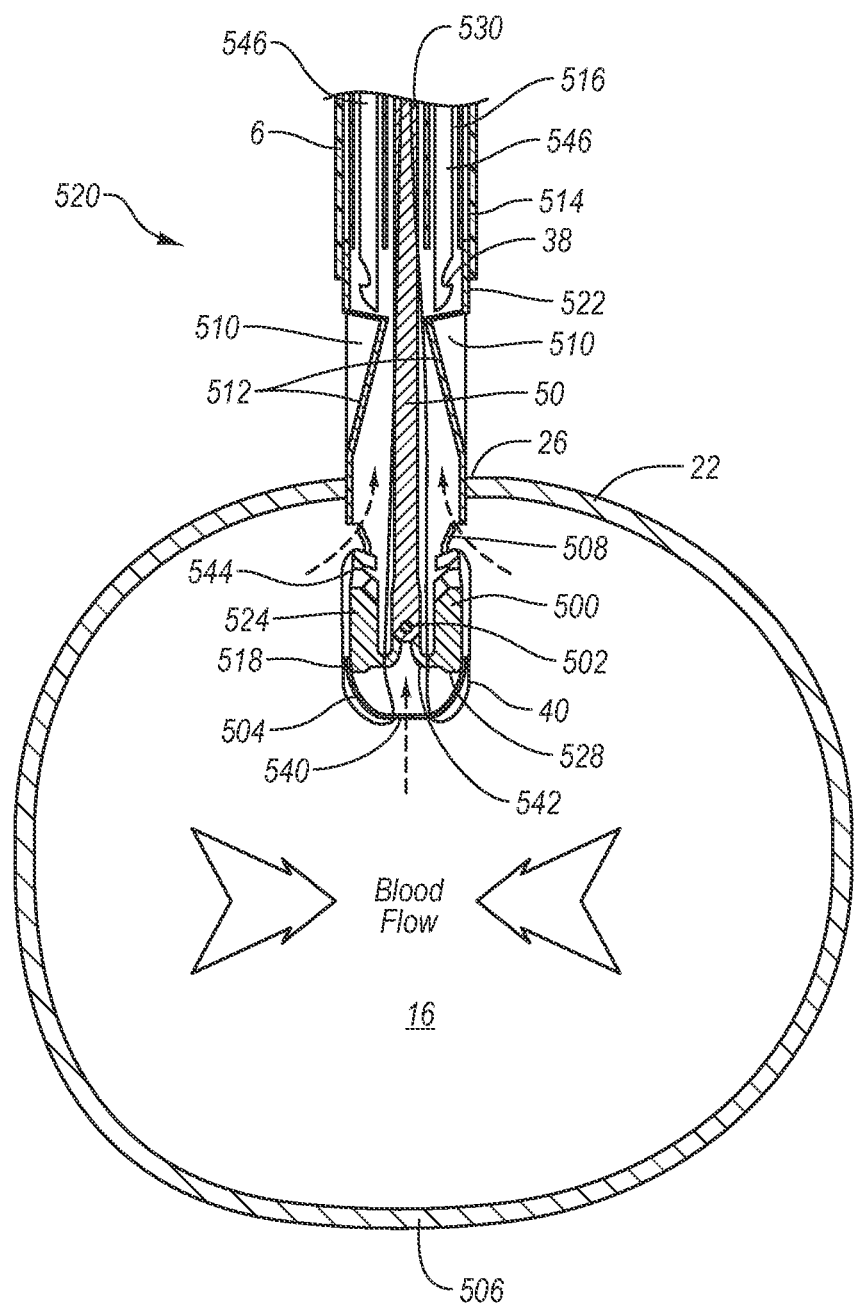
FIG. 1 is a cross-sectional view of a suturing system with its distal end inserted through an arterial wall.
Figure 2:
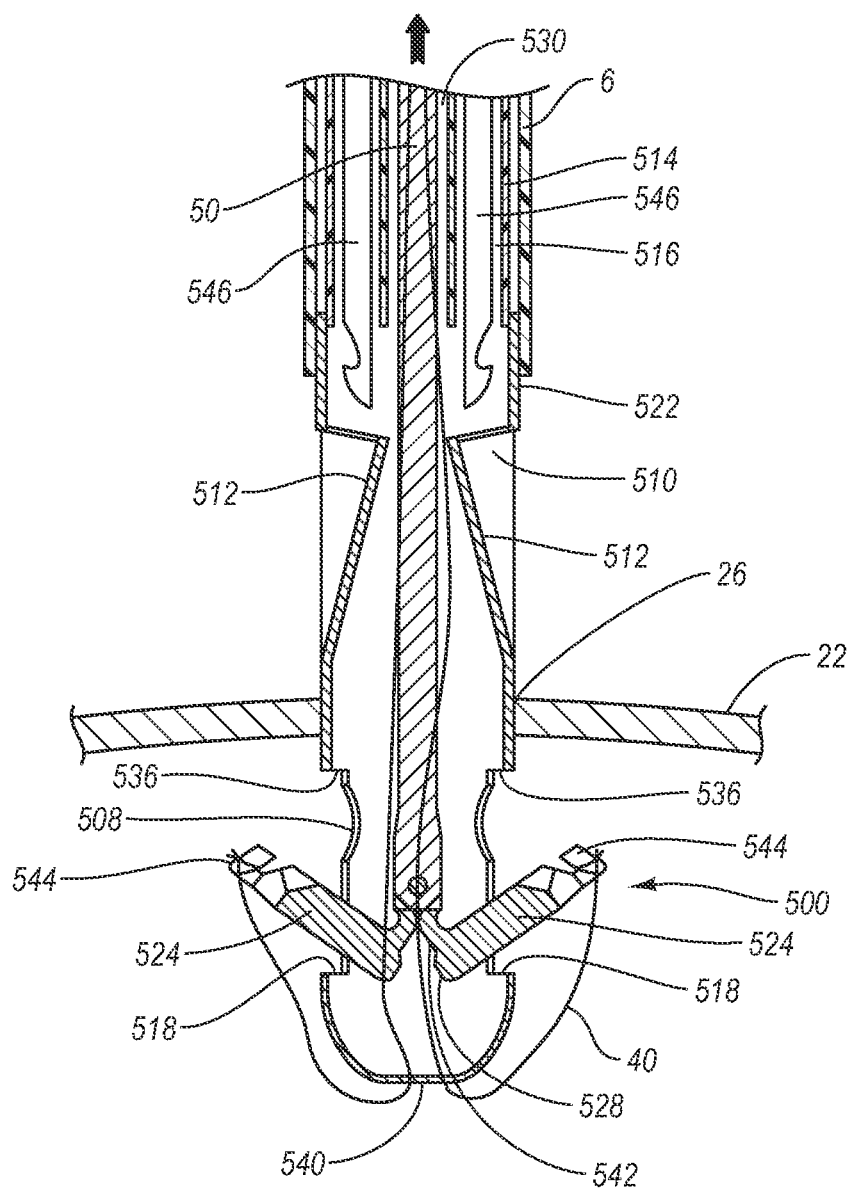
FIG. 2 is a cross-sectional view of the device of FIG. 41 in a partially deployed state.
Figure 3:
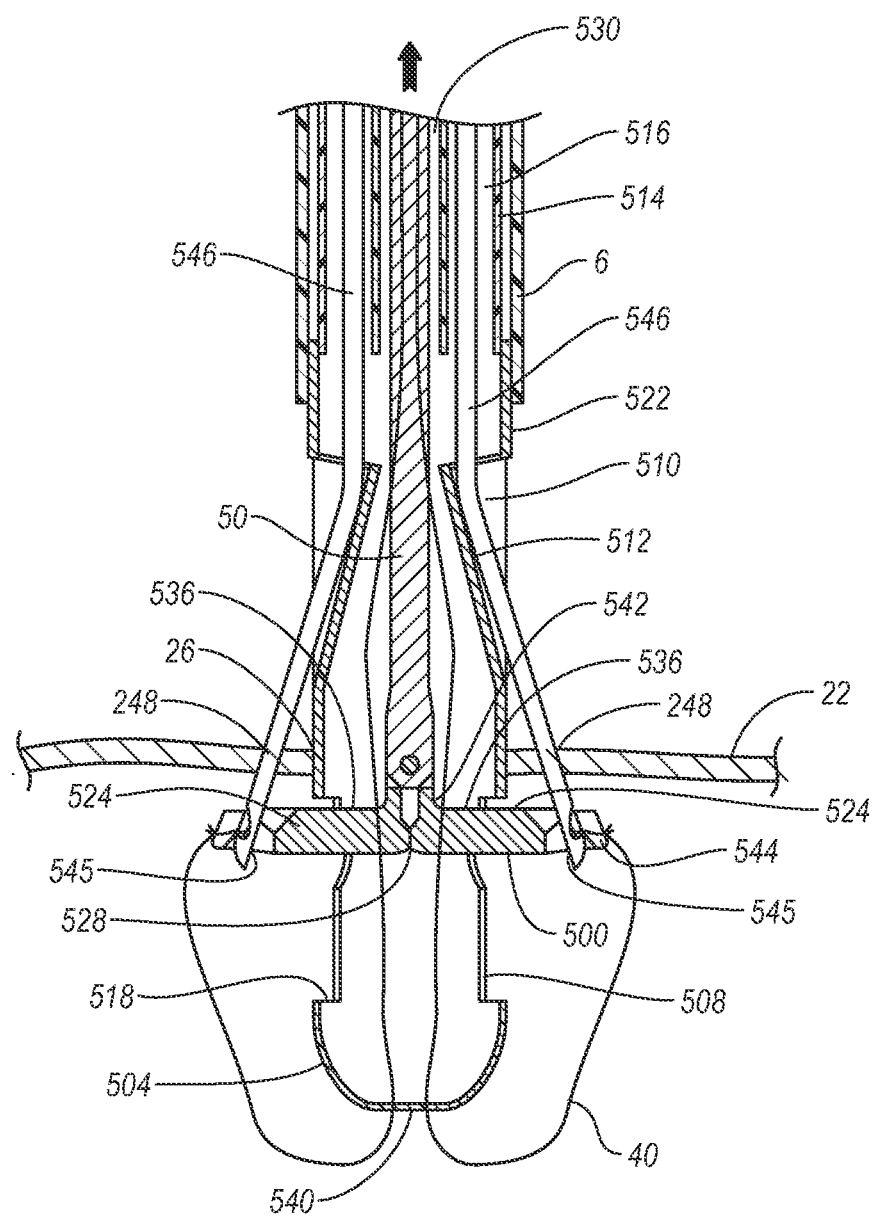
FIG. 3 is cross-sectional view of the device of FIG. 1 with the suture clasp member fully deployed.

FIGS. 1, 2 and 3 show a suturing device corresponding to the suturing device described in U.S. Pat. No. 6,245,079, the complete disclosure of which is incorporated herein by reference in its entirety for all purposes. Specifically, FIGS. 1, 2, and 3 correspond to FIGS. 41, 42 and 47 of U.S. Pat. No. 6,245,079.

Referring to FIG. 1, distal portion of the suturing device 520 is positioned in femoral artery 16. Suturing device 520 comprises a suture introducer head 522 attached to the distal end of a hollow elongated body 514. Suture clasp member 500 and the needles 546 reside in the same longitudinal space. In other words, the needles 546 share the same housing as the suture clasp member 500 (while they are all in their retracted state), but are higher up (proximally) in the suturing device 520 than the suture clasp member 500. Flexible needles 546 bend outward, away from the axis of the device 520, when in the extended position (as shown in FIG. 3).

As shown in FIGS. 2 and 3, the suture introducer head 522 has two needle ports or apertures 510 formed therein (one per needle 546) proximal to the suture clasp arms 524. Each needle port includes a needle guiding portion 512 ("needle guide"), in the form of an outwardly curved groove or channel, which guides the corresponding needle 546 along a particular path. The needle guides 512 may be formed within the suture introducer head 522 (as shown in FIG. 1) as part of a mold, or may be separate pieces (not shown) that are inserted into the suture introducer head 522 during manufacture.

Bleed back is accomplished by the hole 540 at the distal end 504 of the suture introducer head 522, the suture clasp arm apertures 508 and any other openings in the suture introducer head 522. The direction of blood flow for bleed back is shown by the dashed arrows in FIG. 1.

Suture 40 closes the artery vessel opening 26 transverse to the flow of blood. Proper insertion of the needles 546 reduces the risk of damage to the vessel walls 22, 506.

Suturing device 520 includes a single, resilient suture clasp member 500 attached to the actuating rod 50. The suture clasp member 500 comprises a center or hinge portion 542 and two suture clasp arms 524 (one for each needle 546). Each suture clasp arm 524 has a suture clasp 544 at the end thereof.

The hinge portion 542 of the suture clasp member 500 acts as a "living hinge" because it has a memory which causes the member 500 to return to a partially open, unretracted position (FIG. 2) when a force (applied via rod 50) is released. This can be seen in FIGS. 1 and 2. In FIG. 2, the suture clasp member 500 is deployed in the artery 16 in its predisposed (relaxed or natural) position. In FIG. 1, the suture clasp member 500 is retracted into the suture introducer head 522 in its compressed (stressed or tensed) position. The arms 524 are moved to the retracted position by applying a distal force to the actuator rod 50, which causes the arms to contact deflection surfaces 518 (FIG. 2).

This suture clasp member 500 is preferably composed of a resilient shape memory material such as NITENOL, but may alternatively be composed of another material with spring-like characteristics, such as plastic, spring steel, stainless steel or any variations thereof. Further, the suture clasp member 500 could be composed of two arms that are hingedly connected to the actuating rod 50 without the use of a resilient hinge.

Needles 546 are flexible and preferably made from a material with shape memory, such as SUPERFLEX NITENOL. Alternatively, the needles 546 may be composed of spring steel, surgical stainless steel or any variation thereof.

When the needles 546 are advanced distally and come in contact with the needle insertion guides 512, the needle insertion guides cause the needles 546 to bend radially outward. The needles 546 also preferably further bend slightly (radially outward) when they come in contact with the angled surfaces 545 of the suture clasp arms 524, as shown in FIG. 3. When the needles 546 are retracted into the needle lumens 516, they resume a straight configuration as a result of their resiliency.

The proximal portion of the suturing device 520 preferably includes a handle which allows the physician to externally operate the suture clasp arms 524 and the needles 546 inside the blood vessel 16. This handle preferably has three actions: a first action in which the actuating rod 50 applies a proximal force to the hinge portion 542 to deploy and maintain arms 524 in a fully outward position (FIG. 3); a second action to advance the needles 546 distally (FIG. 3) and pull the needles 546 back proximally using one or more springs; and a third action in which the actuating rod 50 applies a distal force to the hinge portion 542 to retract the arms 524 (FIG. 1).

The locked position of the suture clasp arms 524 provides a stable base or foundation for holding the looped ends of the suture 40 while the needles 546 come in contact with the suture clasp arms 524 and capture the suture 40. The suture clasp arms 524 are locked in the locked position by the proximal force of the actuating rod 50, the stationary inside edges 536 of the apertures 508 and the protrusions 528 at the 'elbow' end of each arm 524 (FIG. 3). Specifically, when the suture clasp arms 524 become substantially parallel with each other (i.e., each arm 524 is at an angle of approximately 90 degrees from the actuating rod 50), the protrusions 528 at the 'elbow' end of each arm 524 come into contact with each other and prevent the arms 524 from bending any further than the configuration shown in FIG. 3. The suture clasp member 500 cannot open any farther, even when the needles 546 are inserted distally and come in contact with the suture clasp arms 524. The protrusions 528 prevent the suture clasp member 500 from moving unintentionally (opening any farther) when the needles 546 come in contact with the suture clasp arms 524. This reduces the risk of the looped ends of the suture 40 being accidentally displaced from the suture clasps 544 when the needles 546 engage the suture clasps 544. Thus, the combination of forces asserted by the actuating rod 50, the proximal inside edges 536 of the aperture 508 and the two protrusions 528 sustain the suture clasp arms 524 in a rigid, locked position to facilitate the proper removal of the suture looped ends from the suture clasps 544.

The slits of the suture clasps 544 are angled in a proximal, radially inward direction. Thus, the face of the looped ends of the suture 40 face in a proximal, radially inward direction. In this configuration, there is less chance of the looped ends of the suture 40 falling off the suture clasps 544 improperly or prematurely. When the needles 546 engage the suture clasp arms 524, the only direction the looped ends may move is in a proximal, radially inward direction, which is in the opposite direction of the inserted needles 546. When the needles 546 retract proximally (as shown in FIG. 3), the looped ends reliably fall into the suture catches 38 of the needles 546. It is the proximal movement of the needles 546 which causes the suture catches 38 on the needles 546 to catch the looped ends of the suture 40. This configuration does not rely on a radially outward tension in the looped ends to fasten the looped ends onto the suture catches 38 when the needles 546 are inserted distally.

The description of each of introducer sheath 6, suture catches 38, needle incisions 248, pivot pin 502 and lumen 530 is provided by reference to identically numbered elements in U.S. Pat. No. 6,245,079.

A first important disadvantage of the suturing system illustrated in FIGS. 1, 2 and 3 is that both of the arms 524 deploy to a position that is exactly 90 degrees from the axis of suturing device. This is because protrusions 528 abut one another when suture clasp 500 is fully opened (as shown in FIG. 3). As described above, and in U.S. Pat. No. 6,245,079, it is an advantage of the system of FIGS. 1 to 3 that arms 542 of suture clasp 500 do not open more than 90 degrees to reduce the risk of the looped ends of the suture 40 being accidentally displaced from the suture clasps 544 when the needles 546 engage the suture clasps 544.

Unfortunately, this is particularly problematic when suturing inside a blood vessel, since it may be preferred to enter the blood vessel at a non-perpendicular (e.g.: oblique) angle. In the system of FIGS. 1 to 3, the distal end of the suturing device must therefore be extended to some distance into the blood vessel during operation.

A first feature of the embodiments of the present split arm suturing device is that each of its arms may be extended to different angles from the body of the device. In various embodiments, such angles are non-perpendicular to the longitudinal axis of the suturing device. More particularly, one arm may be extended to a position less than 90 degrees to the body of the device, whereas the other arm may be extended to a position more than 90 degrees to the body of the device.

A second feature of various embodiments of the present split arm suturing device is that each of its arms may be extended one at a time.

Separately, or taken together, these two features of the present invention provide a system which may be conveniently positioned to enter the blood vessel at a non-perpendicular angle, thus minimizing the potential for damage to the blood vessel, while ensuring proper placement of the suture. Thus, an operator can gain better access to smaller arteries and maintain a smaller elbow height, as compared to the suturing device of FIGS. 1 to 3. Thus, the present independently operable split arm suturing device offers significantly increased flexibility to the operator, as compared to the suturing device of FIGS. 1 to 3.

Figure 4A:
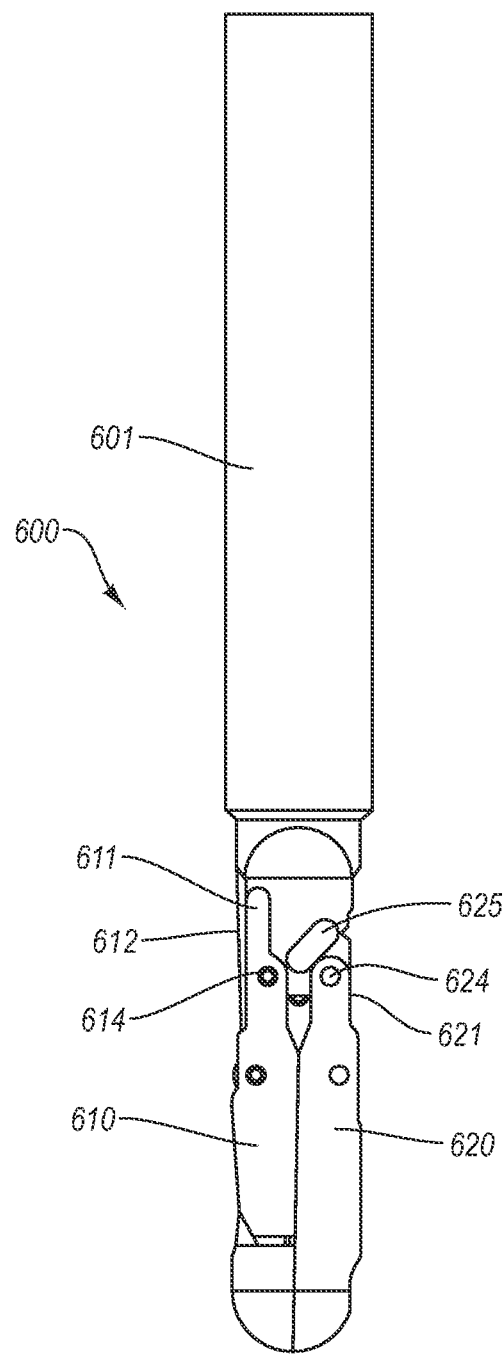
FIG. 4A is a front plan view of the present invention in its compact position (i.e. prior to deployment).
Figure 4B:
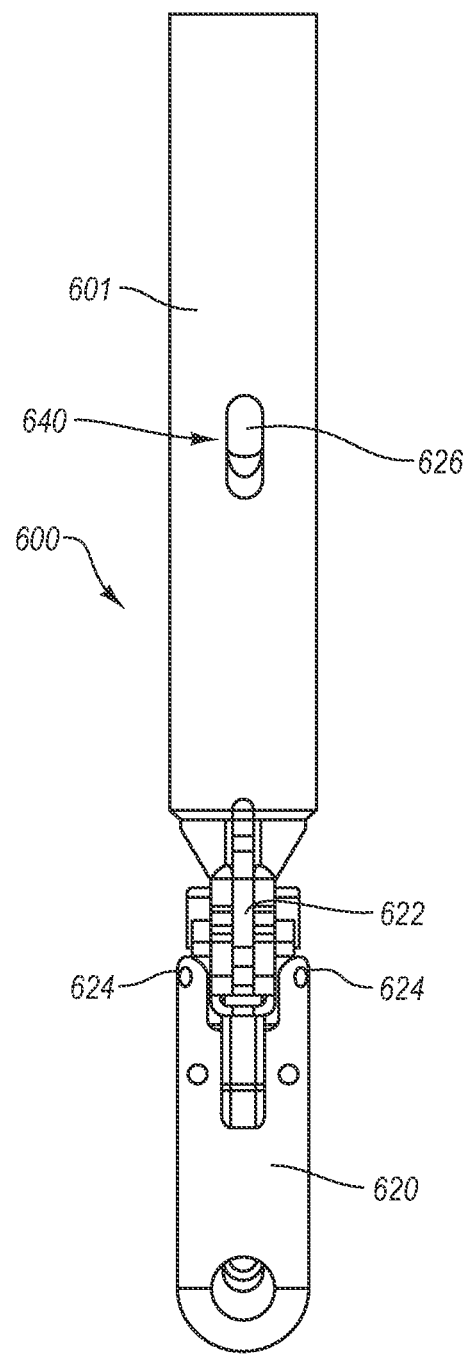
FIG. 4B is a left side elevation view of the present invention prior to deployment.

Referring first to FIGS. 4A and 4B, split arm suturing device 600 is shown prior to deployment (i.e. in its compact position). Suturing device 600 has moveable arms 610 and 620 which can be pivoted relative to the longitudinal axis L of suturing device 600. Arms 610 and 620 may be independently moveable. As will be shown herein, when deployed, arm 610 will preferably be deployed in an anterior direction, and arm 620 will preferably be deployed in a posterior direction.

Figure 5A:
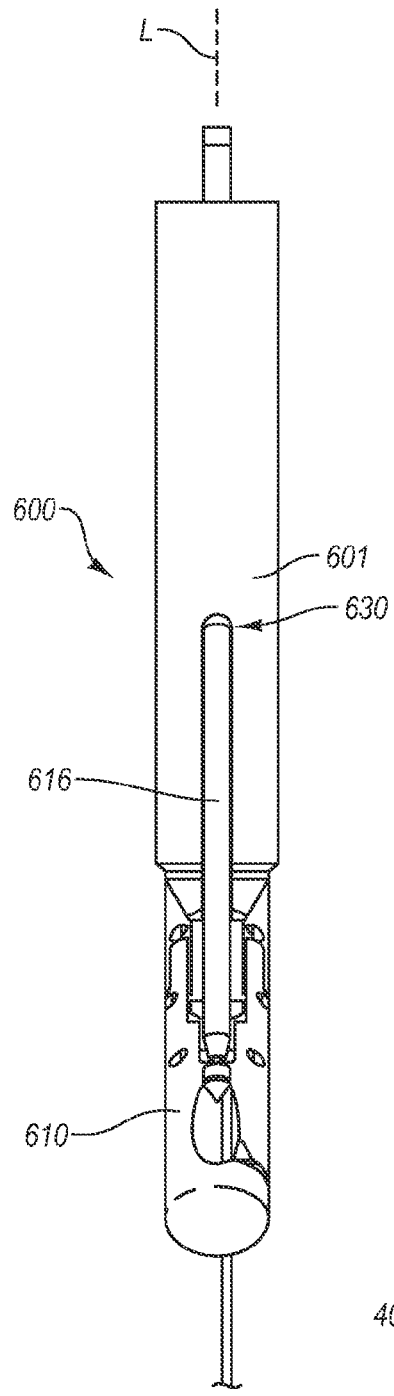
FIG. 5A is a front plan view of the present invention after deployment.
Figure 5B:
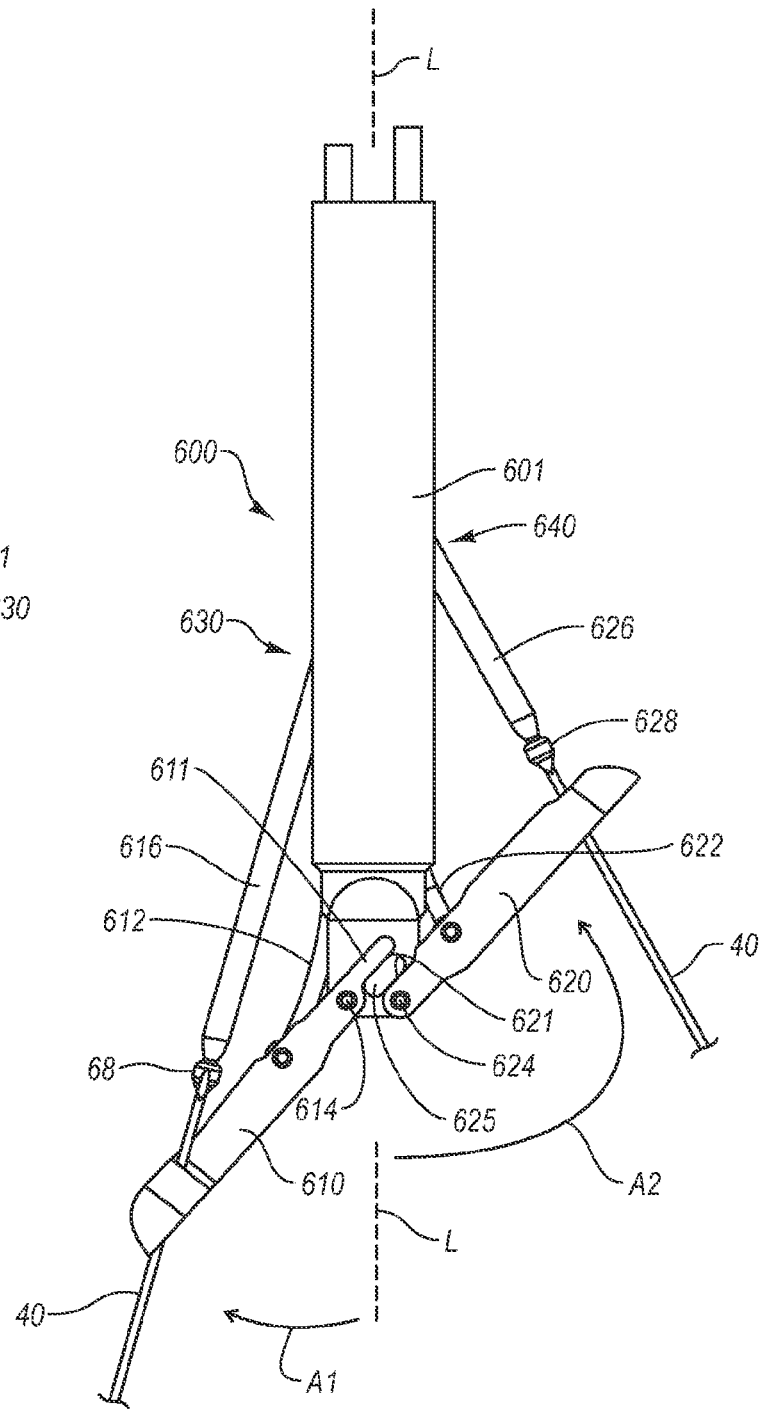
FIG. 5B is a right side elevation view of the present invention after deployment.
Figure 6:
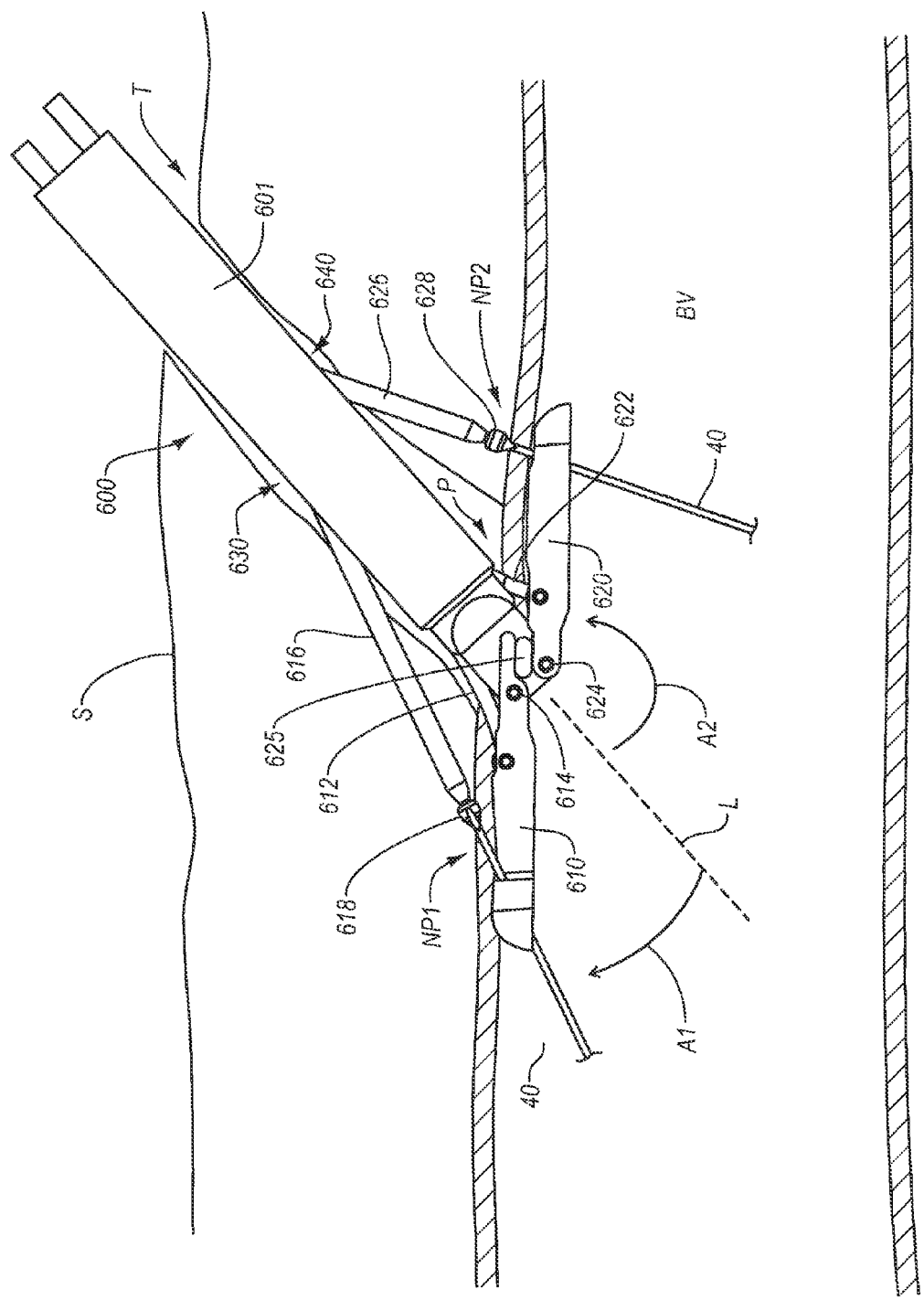
FIG. 6 is an illustration of the system of FIG. 5B deployed at a non-perpendicular angle relative to the axis of a blood vessel while the first and second arms 610 and 620 are positioned longitudinally along the inside of the wall of blood vessel.

Anterior arm 610 and posterior arm 620 may be made independently moveably by any of a variety of mechanisms, all keeping within the scope of the present invention. In the illustrated embodiments, arms 610 and 620 are independently actionable (i.e. moveable between compact and deployed positions) by flexible linkages in tension or compression. It is to be understood, however, that any push pull wire, gear or cam system, or any other suitable actuation system may be used, all keeping within the scope of the present invention. As illustrated in FIG. 5B, arm 610 may be deployed by moving linkage 612, and arm 620 may be deployed by moving linkage 622. Specifically, by pulling linkage 612 proximally, anterior arm 610 rotates around pivot 614 until finger 611 contacts pivot stop 625. Similarly, by pulling linkage 622 proximally, posterior arm 620 rotates (in an opposite direction) around pivot 624 until stop surface 621 contacts pivot stop 625. Specifically, anterior arm 610 moves through angle A1 when moved from its compact position to its deployed position. Referring to FIG. 6, posterior arm 620 moves through angle A2 when moved from its compact position to its deployed position. As can be appreciated, by instead distally pushing linkages 612 and 622, arms 610 and 620 can be moved back to their compact (i.e.: non-deployed) position.

After deploying arms 610 and 620 (by retracting linkages 612 and 622) a first needle 616, and a second needle 626 can then be advanced toward the distal ends of arms 610 and 620, respectively to retrieve opposite ends of a suture 40. In various embodiments, needles 616 and 626 are longitudinally advanceable along the shaft 601 of suturing device 600, and exit through side wall openings 630 and 640 at locations proximal to the arms 610 and 620, respectively.

FIG. 6 shows an embodiment of the present invention deployed at a non-perpendicular angle relative to the axis of a blood vessel BV while the anterior arm 610 and posterior arm 620 are positioned longitudinally along the inside of the wall of blood vessel BV. Specifically, the distal end of suturing device 600 is positioned though a puncture P in blood vessel BV.

Needles 616 and 626 are advanced longitudinally along through shaft, and exit through side wall openings 630 and 640, and then puncture through respective needle punctures NP1 and NP2 in the wall of blood vessel BV. Thereafter, needles 616 and 626 can be retracted pulling the opposite ends of suture 40 upwardly through punctures NP1 and NP2 in the wall of blood vessel BV.

In various embodiments, cuffs 618 and 628 can be provided at opposite ends of suture 40 to ensure that the distal ends of needles 616 and 626 connect securely onto the opposite ends of suture 40. Various embodiments of cuffs, links, barbs, fasteners, or combinations thereof are also contemplated to ensure that the distal ends of needles 616 and 626 connect securely onto the opposite ends of suture 40. Thus, cuffs 618 and 628 may be any of a variety of different designs.

Referring again to FIGS. 5A and 5B, by moving linkages 612 and 622 independently, and to different distances, arms 610 and 620 may be independently deployed to different angles relative to the longitudinal axis L of the body of suturing device 600. For example, as shown in FIGS. 5A and 5B, arm 610 may be rotated less than 90 degrees from the axis of the elongated body of suturing device 600, whereas 620 may be rotated more than 90 degrees from the axis of the elongated body of suturing device 600.

As shown in FIG. 6, this advantageously allows the elongated body of suturing device 600 to be positioned through tissue Tract T (entering through skin S) at a non-perpendicular angle relative to the axis of a blood vessel BV while the first and second arms 610 and 620 are positioned longitudinally along the inside of the wall of blood vessel BV for placement of the suture axially along the blood vessel and across the puncture. Specifically, suturing device 600 can be used to position the ends of suture 40 at locations such that they can be retrieved by needles 616 and 626, and pulled upwardly through needle punctures NP1 and NP2, respectively.

In various embodiments, the elongated body of suturing device 600 is sufficiently rigid to maintain alignment of needles 616 and 626 with arms 610 and 620, respectively. As can be seen, in various embodiments, needles 616 and 626 may be of different lengths.

Figure 7:
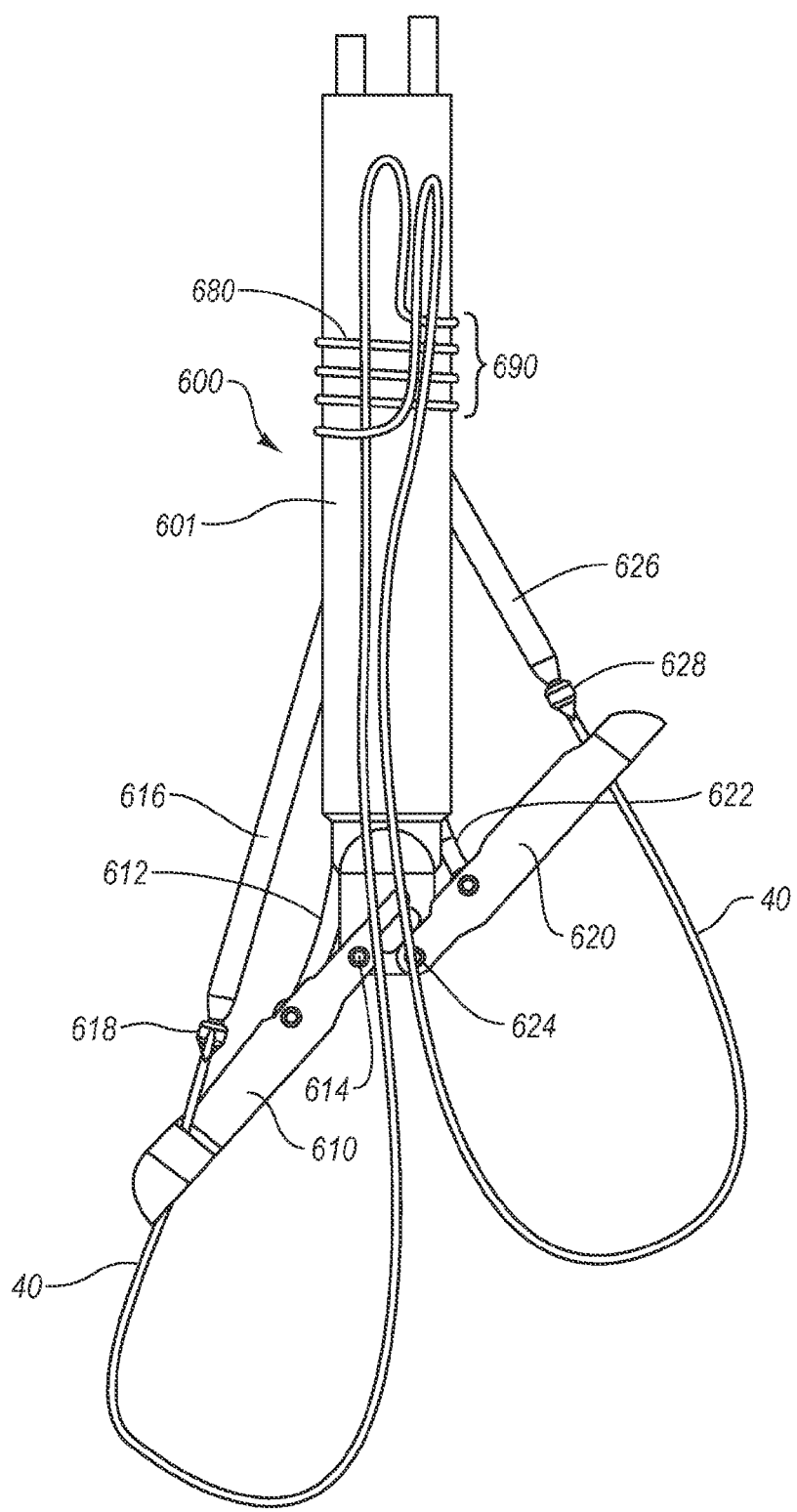
FIG. 7 is an embodiment of the present split arm invention, incorporating a pre-tied knot.

As shown in FIG. 7, a pre-tied knot feature may also be incorporated into suturing device 600. The pre-tied knot may initially be positioned wrapped around an exterior surface of the suturing device. Specifically, a length of suture 40 having opposite ends and a bight 680 of suture therebetween may be provided with bight 680 being disposed around an exterior surface of device 600. Bight 680 may alternately be pre-arranged around one of the needles and within the elongated body.

Bight 680 includes one or more loops of suture that form a pre-tied knot 690 when one or more ends of suture 40 are advanced through bight 680. Bight 680 of suture may be prearranged in any of several configurations on the device. For example, bight 680 may be pre-arranged so as to define a square knot, a clinch knot or a variety of known or new surgical knots.

In various embodiments, suture 40 is arranged to provide the pre-tied knot 680 that automatically travels down from the shaft of the device 600 where it is stored prior to delivery to the tissue wall. In various embodiments, to distinguish the ends of suture 40, during deployment, the ends of the suture may be distinguished from each other by changing the color of one end (e.g. with dye), providing an attachment on one end (e.g. shrink wrap tubing, a bead, etc.) or with the suture itself (e.g. tying a knot in one end).

In accordance with the present invention, suture bight 680 is disposed on the outside surface of device 600, as shown. In this embodiment, suture 40 does not pass through the interior of the device. It should be understood, however, that other embodiments of the invention may include suture 40 and bight 680 stored inside the shaft or housing of the device rather than on the outside. Yet other configurations may include detachable tips and connecting filaments to enable a pre-tied knot.

After needles 616 and 626 retrieve opposite ends of suture 40, and pull these ends of the suture back up through the center of bight 680 to define the pre-tied knot 690, and arms 610 and 620 are rotated back to a non-deployed position, device 600 may be removed from the patient. Pre-tied knot 690 will slide down the shaft, resulting in a suture pattern in which the opposite ends of suture 40 pass upwardly through the center of bight 680.

While embodiments and applications of this invention have been shown and described, it will be apparent to those skilled in the art that various modifications are possible without departing from the scope of the invention. It is, therefore, to be understood that within the scope of the appended claims, this invention may be practiced otherwise than as specifically described.

What is claimed is:

1. A method of suturing a blood vessel, comprising:
advancing a suturing device having an elongated body through a tissue tract, and through an opening in the blood vessel, the tissue tract being situated at a non-perpendicular angle relative to a longitudinal axis of the blood vessel and the suturing device having a longitudinal axis;
extending a first arm at a non-perpendicular angle from the distal end of the elongated body, the first arm having a needle receiving portion thereon;
extending a second arm at a non-perpendicular angle from the distal end of the elongated body, the second arm having a needle receiving portion thereon, wherein the first and second arms extend longitudinally within the blood vessel while the elongated body is positioned within the tissue tract; and
advancing a first needle from a first position adjacent to the elongated body to a second position spaced obliquely outwardly from the first position adjacent to the elongated body, a first needle tip of the first needle being spaced apart from the longitudinal axis a first distance in the first position and a second distance in the second position, the first distance being smaller than the second distance; and
advancing a second needle from a third position adjacent to the elongated body to a fourth position spaced outwardly from the third position adjacent to the elongated body, a second needle tip of the second needle being spaced apart from the longitudinal axis a third distance in the third position and a fourth distance in the fourth position, the third distance being smaller than the fourth distance and the second distance and the fourth distance being different.

2. The method of claim 1, wherein the needle receiving portion of the first arm is dimensioned to receive an end portion of a suture.

3. The method of claim 2, wherein a first end portion of the suture is engaged by the distal end of the first needle.

4. The method of claim 1, further comprising: positioning a loop of suture longitudinally across the opening of the blood vessel to close the opening.

5. The method of claim 1, further comprising: providing a length of suture having two ends and a bight therebetween, the bight prearranged on the device to define a pre-tied knot when the first end portion of the suture is advanced through the bight.

6. A method of suturing a blood vessel, comprising:
advancing a suturing device having an elongated shaft through a tissue tract, and through an opening in the blood vessel, the tissue tract being situated at a non-perpendicular angle relative to a longitudinal axis of the blood vessel and the elongated shaft having a longitudinal axis;
extending a first arm at a non-perpendicular angle from the distal end of the elongated shaft, the first arm having a needle receiving portion thereon;
extending a second arm at a non-perpendicular angle from the distal end of the elongated shaft, the second arm having a needle receiving portion thereon, wherein the first and second arms extend longitudinally within the blood vessel while the elongated shaft is positioned within the tissue tract;
advancing a first needle from a first position adjacent to the elongated shaft to a second position spaced outwardly from the first position adjacent to the elongated shaft, such that the first needle is received into the needle receiving portion on the first arm, a first distance between the first position and the longitudinal axis in a direction transverse to the longitudinal axis being smaller than a second distance between the second position and the longitudinal axis in the direction transverse to the longitudinal axis;
advancing a second needle from a third position adjacent to the elongated body to a fourth position spaced outwardly from the third position adjacent to the elongated body, such that the second needle is received into the needle receiving portion on the second arm, such that a second end portion of the suture is engaged by the distal end of the second needle, wherein a third distance between the third position and the longitudinal axis in a direction transverse to the longitudinal axis being smaller than a fourth distance between the fourth position and the longitudinal axis in the direction transverse to the longitudinal axis, and wherein the fourth distance is different than the second distance.

7. The method of claim 6, wherein the needle receiving portion of the first arm is dimensioned to receive an end portion of a suture.

8. The method of claim 7, wherein a first end portion of the suture is engaged by the distal end of the first needle.

9. The method of claim 6, further comprising: positioning a loop of suture longitudinally across the opening of the blood vessel to close the opening.

10. The method of claim 6, further comprising: providing a length of suture having two ends and a bight therebetween, the bight prearranged on the device to define a pre-tied knot when the first end portion of the suture is advanced through the bight.

11. The method of claim 6, wherein advancing the first needle further comprises advancing the first needle along an angularly orientated needle guiding portion of the elongated shaft to dispose the first needle outwardly from the first position adjacent to the elongated shaft.

12. A method of suturing a blood vessel, comprising:
advancing a suturing device having an elongated shaft through a tissue tract, and through an opening in the blood vessel, the tissue tract being situated at a non-perpendicular angle relative to a longitudinal axis of the blood vessel and the elongated shaft having a longitudinal axis;
extending a first arm at a non-perpendicular angle from the distal end of the elongated shaft, the first arm having a needle receiving portion thereon;
extending a second arm at a non-perpendicular angle from the distal end of the elongated shaft, the second arm having a needle receiving portion thereon, wherein the first and second arms extend longitudinally within the blood vessel while the elongated shaft is positioned within the tissue tract; and
advancing a first needle from a first position adjacent to the elongated shaft to a second position spaced obliquely and longitudinally outwardly from the first position adjacent to the elongated shaft, such that the first needle is received into the needle receiving portion on the first arm, a first distance between the first position and the longitudinal axis in a direction transverse to the longitudinal axis being smaller than a second distance between the second position and the longitudinal axis in the direction transverse to the longitudinal axis; and
advancing a second needle from a third position adjacent to the elongated body to a fourth position spaced outwardly from the third position adjacent to the elongated body, such that the second needle is received into the needle receiving portion on the second arm, such that a second end portion of the suture is engaged by the distal end of the second needle,
wherein a third distance between the third position and the longitudinal axis in a direction transverse to the longitudinal axis being smaller than a fourth distance between the fourth position and the longitudinal axis in the direction transverse to the longitudinal axis, and wherein the fourth distance is different than the second distance.

13. The method of claim 12, wherein advancing the first needle further comprises advancing the first needle along an angularly orientated needle guiding portion of the elongated shaft to dispose the first needle obliquely and longitudinally outwardly from the first position adjacent to the elongated shaft.

* * * * *